United States Patent
Chen et al.

(10) Patent No.: US 7,016,031 B2
(45) Date of Patent: Mar. 21, 2006

(54) SYSTEM AND METHODS FOR CLASSIFYING ANOMALIES OF SAMPLE SURFACES

(75) Inventors: Wayne Chen, Palo Alto, CA (US); Andrew Zeng, Milipitas, CA (US); Mustafa Akbulut, Milpitas, CA (US)

(73) Assignee: KLA-Tencor Corporation, San Jose, CA (US)

(*) Notice: Subject to any disclaimer, the term of this patent is extended or adjusted under 35 U.S.C. 154(b) by 0 days.

(21) Appl. No.: 10/791,026

(22) Filed: Mar. 1, 2004

(65) Prior Publication Data

US 2004/0169852 A1    Sep. 2, 2004

Related U.S. Application Data

(60) Continuation of application No. 10/613,634, filed on Jul. 3, 2003, which is a division of application No. 09/566,352, filed on May 4, 2000, now Pat. No. 6,590,645.

(51) Int. Cl.
*G01N 21/00* (2006.01)

(52) U.S. Cl. ............................ 356/237.2; 356/237.4
(58) Field of Classification Search .. 356/237.1–237.5; 382/145–148
See application file for complete search history.

(56) References Cited

U.S. PATENT DOCUMENTS

| | | | |
|---|---|---|---|
| 4,449,818 A | | 5/1984 | Yamaguchi et al. |
| 5,301,129 A | * | 4/1994 | McKaughan et al. ....... 382/149 |
| 5,699,447 A | * | 12/1997 | Alumot et al. .............. 382/145 |
| 5,808,735 A | * | 9/1998 | Lee et al. ................ 356/237.2 |
| 5,864,394 A | * | 1/1999 | Jordan et al. ............ 356/237.2 |
| 5,907,628 A | | 5/1999 | Yolles et al. |
| 5,991,699 A | * | 11/1999 | Kulkarni et al. .............. 702/83 |
| 6,195,444 B1 | | 2/2001 | Simanovsky et al. |
| 6,201,601 B1 | | 3/2001 | Vaez-Iravani et al. |
| 6,266,437 B1 | | 7/2001 | Eichel et al. |
| 6,271,916 B1 | * | 8/2001 | Marxer et al. ........... 356/237.3 |

OTHER PUBLICATIONS

"Acoustic Scanners and Modulators," M. Gottlieb, Optical Scanning, ed. by Gerald F. Marshall, Dekker 1991, pp. 615-685.

"CMP Applications for Sub-0.25.mu.m Process Technologies," D. Pramanik et al., presented at Electrochemical Society Proceedings: Chemical Mechanical Planarization in IC Device Manufacturing (2.sup.nd International Symposium), vol. 98-7, 1998.

Integrated CMP Defect Monitoring Strategy, W. Chen et al., presented at The Electrochemical Society Proceedings: Chemical Mechanical Polishing in IC Device Manufacturing III, Editors: V.A. Arimoto et la., PV99-37, Honolulu, Oct. 1999.

* cited by examiner

*Primary Examiner*—Michael P. Stafira
(74) *Attorney, Agent, or Firm*—Parsons Hsue & De Runtz LLP (57) ABSTRACT

Two or more defect maps may be provided for the same sample surface at different detection sensitivities and/or processing thresholds. The defect maps may then be compared for better characterization of the anomalies as scratches, area anomalies or point anomalies. This can be done without concealing the more significant and larger size defects amongst numerous small and immaterial defects. One or more defect maps can be used to report the anomalies with classified information; the results from this map(s) can be used to monitor the process conditions to obtain better yield.

66 Claims, 7 Drawing Sheets

Optical Pattern Filtering Defect Detection

FIG._4  Simulated Distribution of Defects After a Scan. Size Indicated in Microns

FIG._5  Initial Clustering in Microscratch Algorithm

Final Output of the Microscratch Algorithm

SYSTEM AND METHODS FOR CLASSIFYING ANOMALIES OF SAMPLE SURFACES

CROSS-REFERENCE TO RELATED APPLICATIONS

This a continuation of application Ser. No. 10/613,364 filed on Jul. 3, 2003, which is a divisional application of application Ser. No. 09/566,352 filed on May 4, 2000, now U.S. Pat. No. 6,590,645. The entire disclosure of prior application Ser. No. 09/566,352 filed on May 4, 2000, is considered as being part of the disclosure of this application and hereby incorporated by reference herein.

BACKGROUND OF THE INVENTION

This invention relates in general to systems for analyzing anomalies of sample surfaces, such as those of semiconductors and those of magnetic or optical disks or flat panel displays, and in particular, to a system for detecting and classifying anomalies of such surfaces.

Achieving the best possible financial performance drives the continuous shrinkage of the critical dimensions of integrated circuit devices that are fabricated on surfaces of semiconductor wafers. This shrinkage requires a flatter wafer surface due to limited lithographic depth of focus (DOF) and higher circuit packing density, along with many other factors. Chemical mechanical planarization or polishing (CMP) has become an enabling technology to fulfill these requirements for the semiconductor industry. Since critical defects scale with the design rule, defect detection tools are required to have better sensitivity; the required sensitivity is roughly half the size of the critical dimension. Unlike many other semiconductor processes, CMP is unique in its requirement that the slurry be both chemically active and mechanically abrasive during polishing. The combination of the chemical reaction and abrasive behavior of the CMP process creates a unique set of defects, such as microscratches, chatter marks, slurry residue, etc. The adoption of CMP presents a great opportunity to have a better DOF budget, but poses a unique challenge in the inspection of processed CMP wafers, along with achieving higher chip yield by using appropriate yield management techniques.

Since CMP has become an essential practice in almost all chip manufacturing with a design rule of 0.25 $\mu$m or smaller, there is an urgent need to have a set of metrology tools that can not only detect but also classify those defects. In general, different types of defects have different sources and different impacts on the final device yield. Classifying them in real time will significantly reduce the time-to-results. The shrinkage of the dimensions of devices leads to an increase of the density of chips that can be produced on a wafer; therefore, more value has been produced from each wafer. This places ever-greater demands on yield management and in particular on defect inspection and classification during the CMP process; the loss of a single production wafer leads to a significant revenue loss. Driven by having shorter time for achieving and maintaining high-yield for high-value added products, the ideal defect inspection system should be able to deliver the necessary information to have a more comprehensive solution, which includes detecting all types of defects, classifying them, analyzing them, and recommending corrective actions.

Unlike particles, some of the CMP-induced defects, such as microscratches and chatter marks, cannot be removed by post-CMP cleaning and it is important to sort them out and minimize their occurrence since they may impact yield. For the cleanable defects such as particles, which may have no significant impact on the final yield, the classified defect counts will be used for process control.

Due to the nature of the process, CMP microscratches are very difficult, if not impossible, to avoid. The larger particles in the slurry or fall-on particles from the pad conditioner mainly induce this type of defect. Depending upon their dimensions and locations, these defects may adversely affect the yield of the device. Needless to say, detecting and classifying these defects will be essential for the desired process monitoring and control for achieving the best possible yield of a production line.

Typical CMP-induced defects can be divided into two categories: extrinsic defects, which are the result of the presence of foreign materials, and intrinsic defects, which are the imperfections created on the polished material. Extrinsic defects include slurry residue, surface particles, and embedded particles. Intrinsic defects include such defects as microscratches, chatter marks, water marks, long scratches (continuous and spiral), pits, rip-out and dishing. Due to the complexity of the patterned wafers, additional types of defects are present. These defects are related to the manufacturing process.

As the name implies, residual slurry results from incomplete or improper cleaning after the CMP step. Surface particles could be picked up from anywhere and are not necessarily CMP related. Embedded particles may result from existing surface particles, abraded film particles, flakes or particles from the slurry that are ground in by the down force of the polishing head.

The relative motion of the wafer and the pad produces a microscratch, when larger particles are present in the slurry. In particular, slurry particles larger than 1 $\mu$m in size can be significant contributors to microscratch generation. Other factors that contribute to microscratch generation include unsuitable rinsing and buffing steps following the CMP step. Although buffing with soft pads over hard pads reduces the formation of microscratches, incorrect buffing produces worse results. The dilute-HF dip step, which follows the buffing polish step, can increase the number of microscratches, enlarges existing microscratches, and leads to failure of the device.

The Surfscan SP1$^{TBI}$® wafer inspection system from KLA-Tencor Corporation, the assignee of the present application, has been used for inspecting unpatterned semiconductor wafers. This system has very high sensitivity and can classify large scratches, such as scratches longer than 1500 nm. However, many scratches produced during the CMP processors are smaller than that and may even be smaller than the spot size of the laser beam used in the system. Scratches that are shorter than a predetermined length such as 1500 nm are referred to herein as "microscratches." Most of the microscratches may be smaller than the spot size of the laser beam used in the Surfscan SPI$^{TBI}$® system, so that they appear as light point defects (LPDs). Therefore, without using a classification method, the user would not be able to distinguish between microscratches from particles or other types of point anomalies such as pits on the wafer surface.

In order to distinguish such microscratches from other point defects such as particles and pits, tools such as scanning electron microscopes or atomic force microscopes have been used. When there are a large number of defects on the wafer surface, such method is time consuming and not practical for use in a production environment. It is, therefore, desirable to provide an improved system for classifying anomalies of a surface in which the above-described difficulties are not present.

SUMMARY OF THE INVENTION

This invention is based on the observation that, by varying the sensitivity by which the anomalies are detected to provide output(s) or by varying a threshold when data on the anomalies are analyzed, more information useful for classifying the anomalies becomes available. By using outputs obtained at two or more different detection sensitivities, or by processing the data on the anomalies using two or more different thresholds, it is possible to distinguish between microscratches and particles, pits or other point defects. At least one classification of the anomalies may then be provided. Preferably, this can be done without requiring a user to scan the sample surface more than one time. This will permit a user to distinguish between microscratches from particles and other point defects and adjust the CMP or cleaning process in real time in an on-line production process or post-processing as required to improve yield.

BRIEF DESCRIPTION OF THE DRAWINGS

For simplicity in description, identical components are identified by the same numerals in this application.

DETAILED DESCRIPTION OF THE EMBODIMENT

As noted above, the Surfscan SPI$^{TBI}$® instrument available from the assignee of the present application, KLA-Tencor Corporation, may be used for inspecting semiconductor wafer surfaces, such as those of unpatterned wafers, as well as other sample surfaces, such as those of magnetic or optical disks for storage and flat panel display type devices. A description of such system is set forth in U.S. patent application Ser. No. 08/933,771, filed on Sep. 19, 1997, entitled "Improved Sample Inspection System." This application is incorporated herein by reference in its entirety, and is referred to herein as the companion application. While the description below of the Surfscan SPI$^{TBI}$® instrument taken from such application describes anomaly detection of semiconductor wafer and film surfaces, it will be understood that essentially the same instrument and process may be used for defect detection of other samples such as magnetic or optical disks used for information storage and flat panel display type devices.

Figure 1:
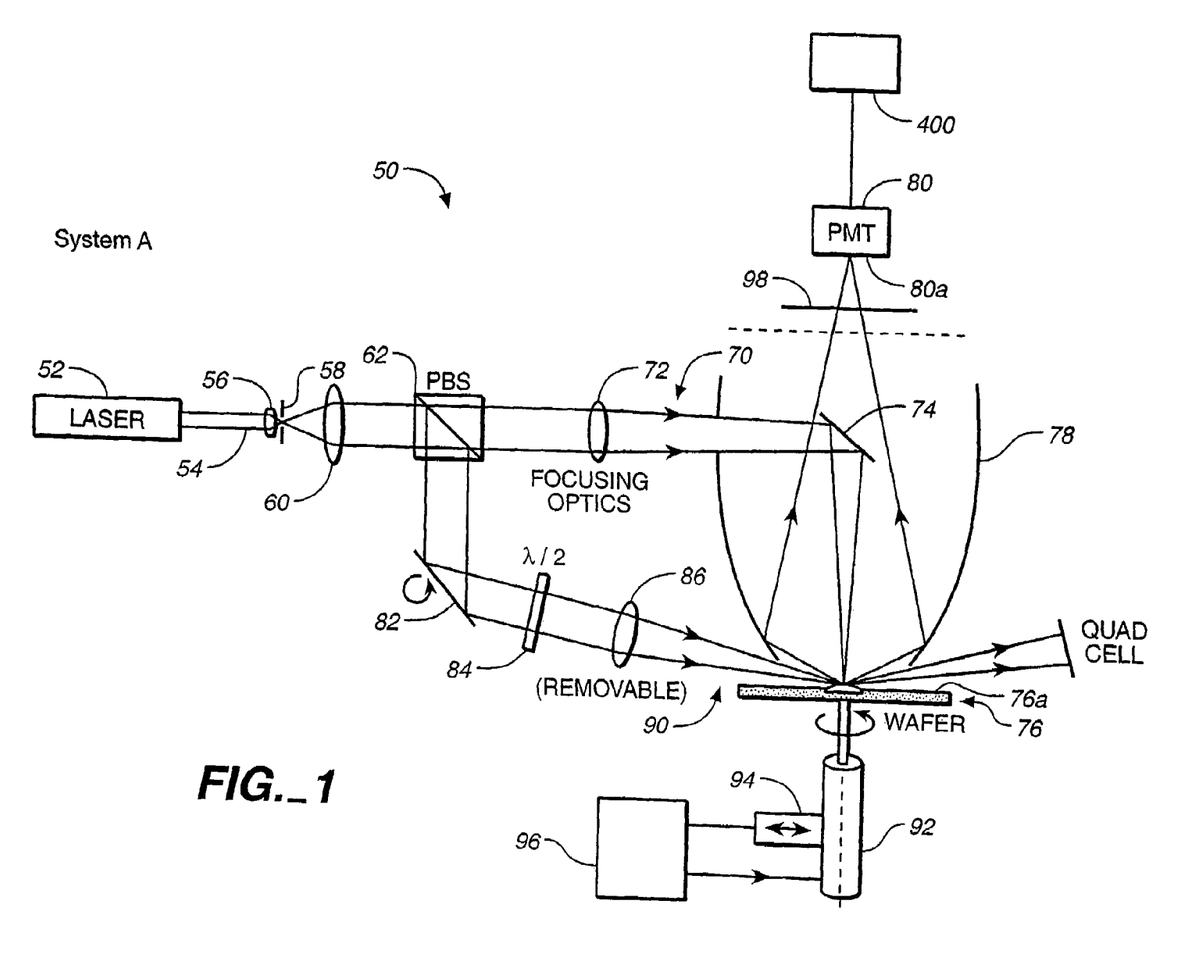
FIG. 1 is a schematic view of a sample inspection system employing a substantially normal channel and an oblique channel useful for illustrating the invention.

Inspecting a sample surface with oblique and/or normal illumination beams can be implemented in a number of ways. FIG. 1 is a schematic view of a sample inspection system 50 to illustrate a general set up for implementing anomaly detection using both normal and oblique illumination beams. A radiation source that provides radiation at one or more wavelengths in a wide electromagnetic spectrum (including but not limited to ultraviolet, visible, infrared) may be used, such as a laser 52 providing a laser beam 54. An electron beam or the like can be used as the radiation source as well. A lens 56 focuses the beam 54 through a spatial filter 58 and lens 60 collimates the beam and conveys it to a polarizing beamsplitter 62. Beamsplitter 62 passes a first polarized component to the normal illumination channel and a second polarized component to the oblique illumination channel, where the first and second components are orthogonal. In the normal illumination channel 70, the first polarized component is focused by optics 72 and reflected by mirror 74 towards a sample surface 76a of a semiconductor wafer 76. The radiation scattered by surface 76a is collected and focused by an ellipsoidal mirror 78 to a photomultiplier tube 80.

In the oblique illumination channel 90, the second polarized component is reflected by beamsplitter 62 to a mirror 82 which reflects such beam through a half-wave plate 84 and focused by optics 86 to surface 76a. Radiation originating from the oblique illumination beam in the oblique channel 90 and scattered by surface 76a is collected by an ellipsoidal mirror and focused to photomultiplier tube 80. Photomultiplier tube 80 has a mask or pinhole entrance 80a. The mask or pinhole 80a and the illuminated spot (from the normal and oblique illumination channels on surface 76a) are preferably at the foci of the ellipsoidal mirror 78.

Wafer 76 is rotated by a motor 92 which is also moved linearly by transducer 94, and both movements are controlled by a controller 96, so that the normal and oblique illumination beams in channels 70 and 90 scan surface 76a along a spiral scan to cover the entire surface.

As described in the companion application, scattered radiation from the wafer surface originating from the normal illumination path and from the oblique illumination path may be distinguished in a number of different ways, such as by using different polarization or wavelength of light in the two different channels.

For patterned semiconductor wafers, the AIT II tool is a laser scanning inspection system from the assignee of the present application, KLA-Tencor Corporation, which may be used when inspecting such surfaces. A description of such system is set forth in U.S. Pat. No. 5,864,394, which is incorporated herein in its entirety by reference. While the description below of the AIT II instrument taken from such patent describes anomaly detection of semiconductor wafer surfaces, it will be understood that essentially the same instrument and process may be used for defect detection of other samples such as magnetic or optical disks used for information storage and flat panel display type devices, or photomask or ceramic tile.

Figure 2:
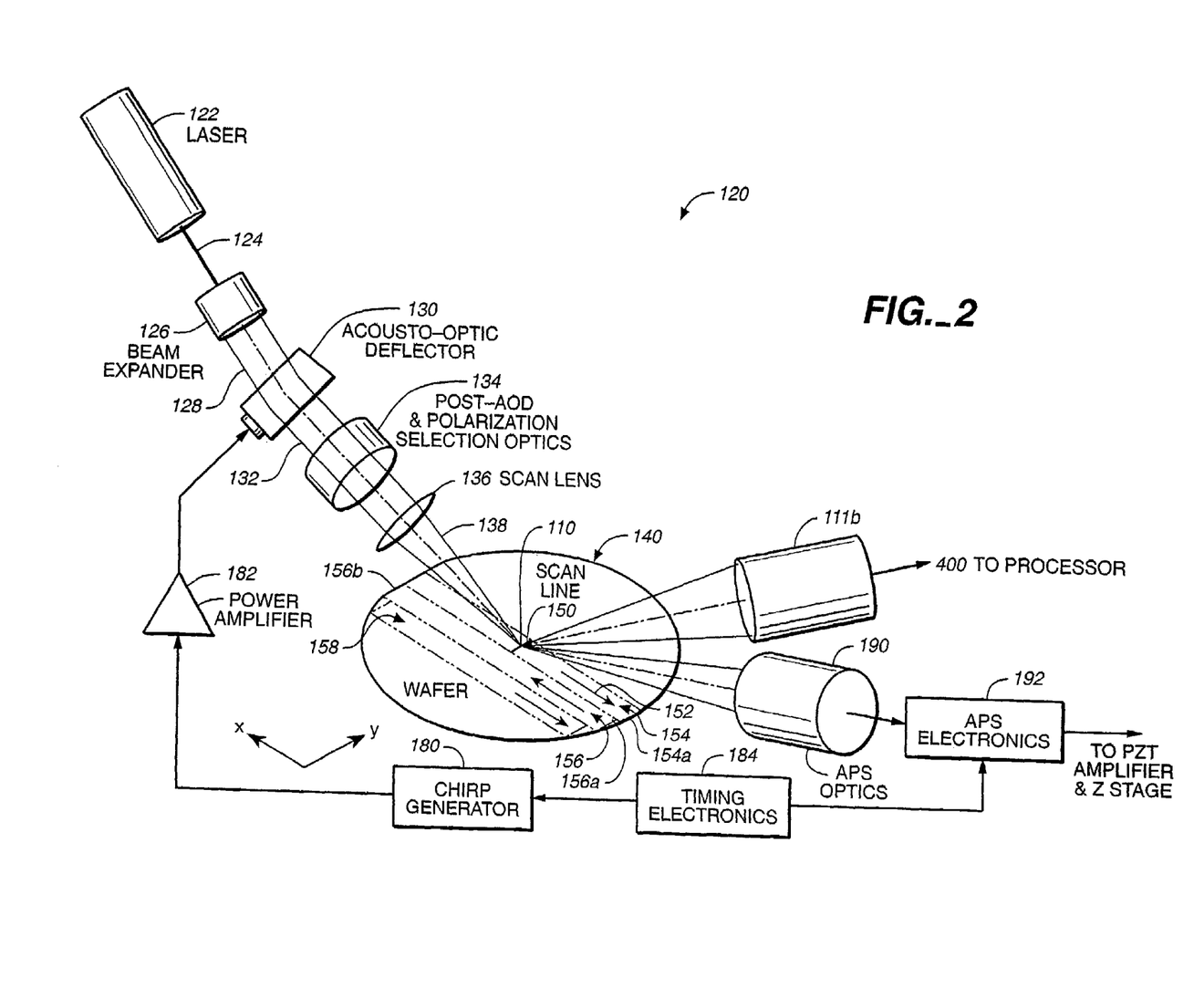
FIG. 2 shows partially in perspective and partially in block diagram form a system for inspecting anomalies of a patterned semiconductor wafer surface useful for illustrating the invention.

Another surface inspection system of this application will now be described in reference to FIG. 2. As shown in FIG. 2, system 120 includes a laser 122 providing a laser beam 124. Beam 124 is expanded by beam expander 126 and the expanded beam 128 is deflected by an acousto-optic deflector (AOD) 130 into a defected beam 132. The deflected beam 132 is passed through post-AOD and polarization selection optics 134 and the resulting beam is focused by telecentric scan lens 136 as a focused beam 138 onto a spot 110 on surface 140 to be inspected, such as that of a semiconductor wafer, photomask or ceramic tile, patterned or unpatterned.

In order to move the illuminated area that is focused onto surface 140 for scanning the entire surface, The AOD 130 causes the deflected beam 132 to change in direction, thereby causing the illuminated spot 110 on surface 140 to be scanned along a sweep 150. As shown in FIG. 2, sweep 150 is preferably a straight line having a length which is smaller than the dimension of surface 140 along the same direction as the sweep. Even where sweep 150 is curved, its span is less than the dimension of surface 140 along the same general direction. While the illuminated spot is scanning surface 140 along sweep 150, surface 140 of the wafer is moved by an XY stage (not shown) along the X axis so that the illuminated area of the surface moves along arrow 152 and AOD 130 causes the illuminated spot to scan a sweep 152 parallel to sweep 150 and in an adjacent position spaced apart from sweep 150 along the negative X axis. As the illuminated spot covers said sweep, surface 140 is moved by a small distance so that the area of the surface to be illuminated is moved along direction 152 in order to scan an adjacent sweep at a different X position. As described in U.S. Pat. No. 5,864,394, this small distance is preferably equal to about one quarter of the dimension of spot 110 in the X direction. This process is repeated until the illuminated spot has covered strip 154, at this point in time the illuminated area is at or close to the edge 154a. At such point, the surface 140 is moved by the XY stage along the Y direction by about the length of sweep 150 in order to scan and cover an adjacent strip 156, beginning at a position at or close to edge 156a. The surface in strip 156 is then covered by short sweeps such as 150 in a similar manner until the other end or edge 156b of strip 156 is reached at which point surface 150 is again moved along the Y direction for scanning strip 158. This process is repeated prior to the scanning of strip 154, 156, 158 and continues after the scanning of such strips until the entire surface 140 is scanned. Surface 140 is therefore scanned by scanning a plurality of arrays of sweeps the totality of which substantially covers the entire surface 140.

The deflection of beam 132 by AOD 130 is controlled by chirp generator 180 which generates a chirp signal. The chirp signal is amplified by amplifier 182 and applied to the transducer portion of AOD 130 for generating sound waves to cause deflection of beam 132 in a manner known to those skilled in the art. For a detailed description of the operation of the AOD, see "Acoustooptic Scanners and Modulators," by Milton Gottlieb in Optical Scanning, ed. by Gerald F. Marshall, Dekker 1991, pp. 615–685. Briefly, the sound waves generated by the transducer portion of AOD 130 modulate the optical refractive index of an acoustooptic crystal in a periodic fashion thereby leading to deflection of beam 132. Chirp generator 180 generates appropriate signals so that after being focused by lens 136, the deflection of beam 132 causes the focused beam to scan along a sweep such as sweep 150 in the manner described.

Chirp generator 180 is controlled by timing electronic circuit 184 which in the preferred embodiment includes a microprocessor. The microprocessor supplies the beginning and end frequencies f1, f2 to the chirp generator 180 for generating appropriate chirp signals to cause the deflection of beam 132 within a predetermined range of deflection angles determined by the frequencies f1, f2. The autoposition sensor (APS) optics 190 and APS electronics 192 are used to detect the level or height of surface 140. Detectors such as detectors 110a, 110b, 111a, 111b of FIG. 2 collect light scattered by anomalies as well as the surface and other structures thereon along sweep 150 and provide output signals to a processor (not shown, which may be a set of processors, one for each detector) in order to detect anomalies and analyze their characteristics.

The systems in FIGS. 1 and 2 described above are what is known as dark field systems, where the radiation scattered by the anomalies and collected for detection is in directions away from the specular reflection direction of the illuminating beam. Anomaly information may also be obtained by a different type of system known as imaging detection systems, such as that shown in FIG. 3.

Figure 3:
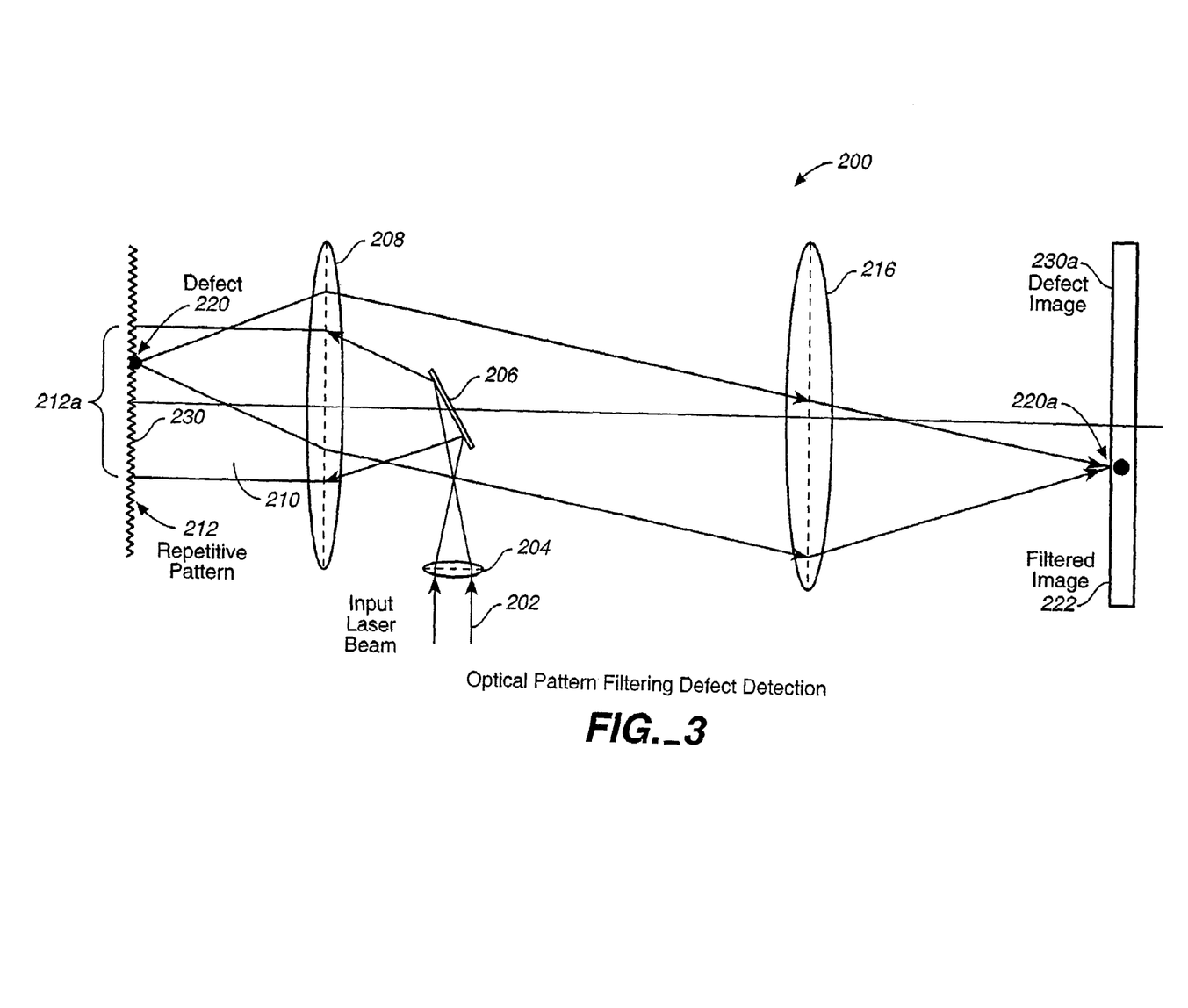
FIG. 3 is a cross-sectional view of an imaging type defect detection system useful for illustrating the invention.

As shown in FIG. 3, the input laser beam 202 of the imaging detection system 200 is focused by a lens 204, reflected by mirror 206 and then collimated by lens 208 to sample surface 210, which may include a repetitive pattern, or be an unpatterned surface. Different from the dark field systems of FIGS. 1 and 2, the area of surface 212 illuminated by the collimated beam 210 is typically much larger than that of the dark field systems of FIGS. 1 and 2. The illumination scheme in the imaging system of FIG. 3 is known in the industry as flood illumination. Thus, the area 212a of sample surface 212 illuminated by beam 210 may contain many defects. Lenses 208 and 216 focus light scattered by a defect such as defect 220 to a corresponding spot of an image plane 222 of lenses 208, 216, forming an image 220a of the defect 220 in the image plane 222. Typically, an array of charged coupled devices (CCDs) is placed in the image plane so that the defect image 220a falls on a corresponding CCD in the array.

As noted above, area 212a is large and may contain more than one defect, such as defect 230. Light scattered by defect 230 in area 212a is also focused by lenses 208 and 216 onto the image plane but at a different location than defect image 220a, such as defect image 230a, shown in FIG. 3. Since the detector in the CCD array detecting the scattered light forming the defect image 230a is different from the detector detecting the defect image 220a, the two defects 220 and 230 can be differentiated and the resolution of the system depends on the collection optics and the spatial resolution of the CCD array and not on the optics illuminating sample surface 212. This is in contrast to the dark field systems of FIGS. 1 and 2, where the illumination beam is focused onto a small spot typically of several to tens of microns in cross-sectional dimensions, where the signal-to-noise ratio is improved by reducing the spot size. In system 200, as noted above, the resolution is controlled by the collection optics (such as lenses 208, 216) and the spatial dimensions and speed and time of signal accumulation of the detector array.

Figure 4:
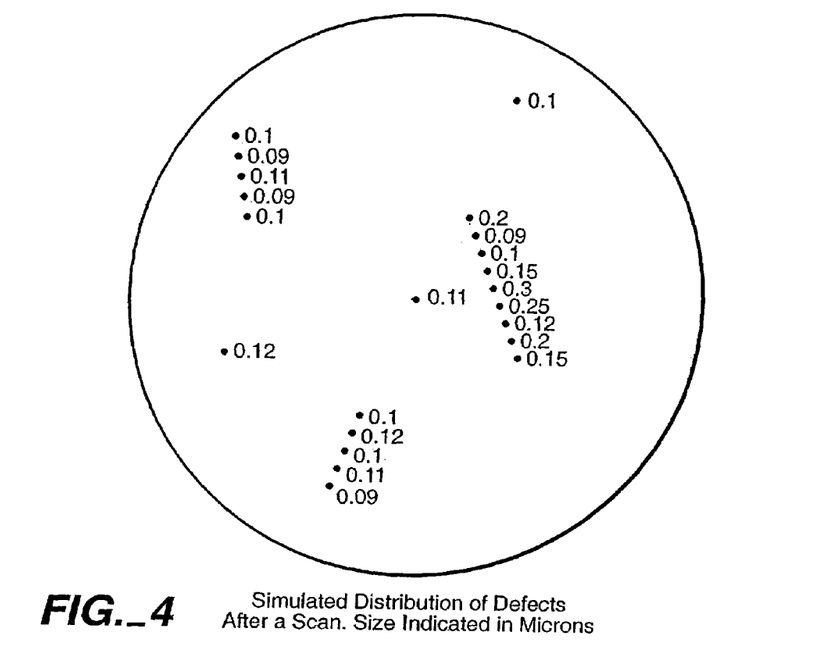
FIG. 4 is a schematic view of a simulated distribution of anomalies from a detection system such as those shown in FIGS. 1–3 and 10, where size of the anomaly is indicated in microns.

Beam 210 is caused to scan the surface 212 by causing relative motion between the sample surface 212 and the beam, so that a defect map of sample surface 212 is obtained in a manner known to those skilled in the art. As described above, the dark field systems of FIGS. 1 and 2 scan the entire surface of the sample and provide defect maps of the sample. FIG. 4 is a schematic view of a simulated distribution of anomalies from a detection system such as those shown in FIGS. 1–3 and 10 (to be described below), where the size of each anomaly is indicated in microns.

The detection systems such as those shown in FIGS. 1–3 and 10 employ detectors that convert radiation scattered or reflected by anomalies towards detectors that convert such radiation signal to electrical signals. The electrical signals are then processed by a processor which may be a digital signal processor, microprocessor, programmable logic or other processing circuits. The processor will then process the signals from the detectors to analyze and classify the anomalies. The combined inspection and processor system has an inherent noise level. Noise can also be caused by stray radiation collected and detected by the detector where the stray radiation did not originate from the anomalies. Optical imperfections, variations in the illumination intensity and other environmental factors may also affect the noise level in the inspection/processor system. Therefore, there is an inherent noise level which sets the limits for detection and classification of anomalies.

In one way to increase the amount of information obtained from the inspection/processor system, the sensitivity of the detector can be set to the highest value. As noted above, the detectors used in the systems of FIGS. 1–3 and 10 include photomultiplier tubes, photodiodes and CCD arrays. In all of these detectors, signal-to-noise ratio can be improved by increasing the time of detection. Since the noise signals collected by the detectors are substantially of a random nature whereas the signals containing information concerning the anomalies are not, by collecting the radiation signals for a longer period of time, the effect of the random signals will tend to cancel whereas the signals containing anomaly information would not, thereby increasing the signal-to noise ratio. It is also possible to increase gain control to increase detection sensitivity. Thus, gain control can be increased to the maximum in the photomultiplier tube to provide the maximum amplitude electrical signal in response to the detection of radiation signals.

In the processor that processes the electrical signal provided by the detectors to analyze and classify the anomalies, there is a noise level of the combined detector and processor system, where only signals of amplitudes above this noise level may be processed to yield useful information concerning the anomalies.

Another possible limitation is the processing speed of the processor of data concerning anomalies from the detector where the result of the analysis and classification should be available on a real time or substantially real time basis. Thus, where the invention of this application is applied to detecting and classifying anomalies on a semiconductor wafer, a certain amount of time is required to remove the wafer that has been inspected and replace it with one that has not been in order to perform anomaly detection in an online production process of electronic devices. If the speed of the processor is fast enough to analyze and classify the anomalies on one wafer that has been inspected before or not long after inspection data of the next wafer reaches the processor, there is no need to significantly slow down the production process in order to accommodate the speed of the processor. In such circumstances, the processor is able to analyze and classify the anomalies on a real time or substantially real time basis.

In order to obtain the maximum information by means of the detection systems of FIGS. 1–3 and 10, it is preferable to set the sensitivity of the detection system to the highest level. This may mean, for example, setting the gain of the photomultiplier tube to the highest level, and collecting radiation from the anomalies and detecting the collected radiation for as long as would be practical for the user. When applied in a production process, for example, where results of the analysis and classification are desirable on a real time or substantially real time basis, the collection time may be set to a maximum value while avoiding significant delays in the production process.

In the processor processing the output of the detector in FIGS. 1–3 and 10, a signal threshold is typically set at a level that is above the system noise level for analysis of the detector output. To obtain the maximum information concerning the anomalies from the detector output, it would be desirable to set the threshold to as low a level as possible above the noise level. Again, when applied in an online production process where analysis and classification of the anomalies is desired on a real time or substantially real time basis, such threshold is preferably set as low as possible without delaying the production process. Where the detector output is stored and processed on a non-real time basis, the threshold may be set at a level which is slightly above the noise level, for example.

In existing anomaly inspection systems, the sensitivity of the detector and/or the threshold of the processor may not have been set to provide the maximum information, since such information may overwhelm the user. For example, if certain small size defects do not significantly affect the yield of certain electronic devices fabricated from the wafer, the user may not wish to be aware of such anomalies. Furthermore, where anomaly information is provided in the form of a wafer map, for example, the presence of information on a large number of immaterial small size anomalies may render it difficult for the user to discover and focus on the larger sized anomalies which do affect yield. For this reason, in conventional anomaly detection systems, the sensitivity of the detector and/or the threshold of the processor may not have been set to provide the maximum information, since such information may conceal the really significant anomalies that are of concern amongst thousands of immaterial small anomalies.

As noted above, the conventional method for defect analysis and classification is by means of optical microscopes, confocal review stations, scanning electron microscopes and atomic force microscopes which are typically very slow. When the large anomalies of concern are present on the wafer map amongst thousands of small anomalies not of concern, it will be difficult to apply such conventional techniques to each of the anomalies. On the other hand, where the sensitivity of the detector and the threshold of the processor are not set to provide the maximum information, it may be difficult for the user to distinguish between a point defect such as a particle from a microscratch. This invention is based on the observation that, by analyzing information on the anomalies at different detector sensitivities and/or processor thresholds, it is possible to distinguish point defects such as particles from microscratches without inundating the user with extraneous and useless information.

Preferably, the sensitivity of the detector is set to the highest level and the processor threshold is set to the lowest possible level to provide the maximum information on the anomalies. The processor then performs an analysis of the detector output to provide a first classification of the anomalies. Then the sensitivity of the detector and/or the threshold of the processor is altered and the detector output is again analyzed and the anomalies classified in a second classification. If the first classification is obtained at the highest sensitivity and the lowest threshold, the second classification would then be obtained at a lower sensitivity and/or higher threshold to screen out extraneous information useless to the user. What appears as point anomalies in the second classification may turn out to be scratches in the first classification. Therefore, while the second classification may be used as the basis of a presentation of sample defects to the user, such as in the form of a wafer map, the second classification may be supplemented or altered using the first classification to provide more accurate information to the user. For example, if what appears to be point anomalies in the second classification are actually scratches in the first classification, then a wafer map may be constructed using the second classification but where the point anomalies in the second classification are altered to indicate microscratches. Such modified and improved wafer map may then be provided to the user. This process is illustrated in reference to FIGS. 4–6 below.

FIG. 4 is a schematic view of a simulated distribution of defects after a scan using any one of the systems of FIGS. 1–3 and 10. Obviously the number of defects or anomalies in actual wafer maps may be much larger than shown in FIG. 4. The size of the defects are shown in microns in FIG. 4. A clustering algorithm is then performed by the processor for grouping the defects together. The algorithms performed by the processor may include Search Distance, Minimum Events, Aspect Ratio (AR) and Minimum Length. If there is a scratch on the sample surface, different portions of the scratch along the length of the scratch may appear as a separate defect in the defect map. In order to identify a scratch, what may appear to be isolated defects or anomalies located in proximity to each other may need to be grouped together first so that a scratch may be identified. This is accomplished by the Search Distance algorithm. In this process, for each defect on the wafer map, the processor searches for one or more defects located within a certain radius from such defect. When such other defect or defects are found, this process is repeated for such defect or defects found and the process continues until no further defect is found within the radius of the last defect. The defects so found then are examined as to whether they are to be grouped together. In reference to group C of FIG. 5, for example, the defect of size 0.11 $\mu$m is found in the Search Distance algorithm to be within a certain set distance from the defect of size 0.09 $\mu$m, using the defect of size 0.09 $\mu$m as center in the algorithm. Then using as the center the defect of size 0.11 $\mu$m, a third defect of size 0.1 $\mu$m is found to be within said radius. This process is repeated until the processor finds the fifth and last defect of size also of 0.1 $\mu$m, after which no further defect is found except for the previously mentioned defects. Additional algorithms are then applied to these five defects to see whether they are to be grouped together.

The combination of the chemical reaction and abrasive behavior of the CMP process may cause a large drop of abrasive solvent to remain on the sample surface, causing a shallow depression on the sample surface that appears in the defect map as a number of defects spread over an area. Or certain droplets of abrasive solvent may land in the vicinity of each other on the wafer surface causing several small defects to be located in the vicinity of each other. It would be useful to be able to distinguish between such defects. Thus, the defects that indicate a shallow depression represent an area anomaly and are preferably grouped together as an area defect. The isolated defects caused by the droplets are individual defects not necessarily correlated with one another, and are preferably not grouped together but remain as individual defects. Then there are the defects that appear as a string that stem from a scratch and are preferably classified as a scratch.

Individual defects can be distinguished from scratches and area anomalies by requiring that a certain minimum number of defects be required to form a scratch or area defect. Therefore, in the above-described process of the Search Distance algorithm if the number of events, defects or anomalies found in the above-described process is less than a certain preset minimum, then the defects may not all originate from a single scratch or area defect, and will not be grouped together. After the Search Distance algorithm has been performed, if the number of such events, defects or anomalies found within a certain distance from at least one other of such events, defects or anomalies in the same process of the Search Distance algorithm exceeds a preset value in the Minimum Events algorithm, the defects are then grouped into groups, such as groups A, C and F in FIG. 5. Thus, if the preset number in the Minimum Events algorithm is four, for example, the five defects found in the above-described process are then grouped together as group C.

Figure 5:
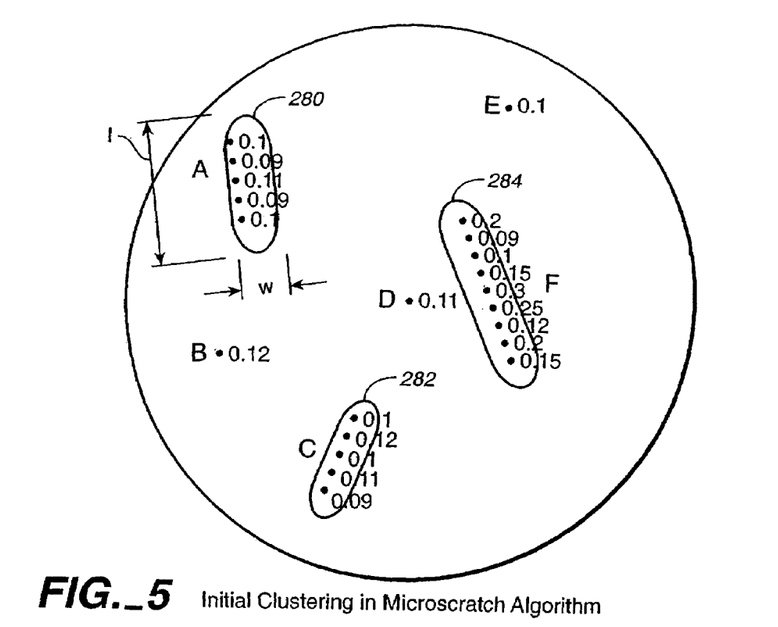
FIG. 5 is a schematic view of the simulated distribution of FIG. 4, where the anomalies have been grouped or clustered using an algorithm of this invention.

In order to distinguish area defects or anomalies from scratches, the processor applies an Aspect Ratio algorithm. In order for a particular group of defects or anomalies to be identified as a scratch instead of an area anomaly, the geographical distribution of defects are preferably such that such geographical distribution is elongated and resembles that of a scratch rather than that of an area. This may be ascertained by drawing a boundary (such as lines 280, 282, 284 in FIG. 5) around the group and computing the ratio of a length l to a width w of the boundary as indicated in FIG. 5. If the ratio is smaller than a certain preset value, then the group of defects forms an area type anomaly rather than a scratch. Thus, for the groups or clusters A–F shown in FIG. 5, where the minimum number of defects required for a scratch or area is set to a value such as 4 and aspect ratio for a scratch set to 3, clusters or groups A, C or F are identified as scratches, whereas groups B, D and E are identified as point or individual defects or anomalies. No area defects are shown in FIGS. 4–6.

For certain semiconductor manufacturers, some of the defects or anomalies shown in FIG. 5 may be too small to be of concern, such as the defect of size 0.1 $\mu$m in group E or the 5 defects of sizes up to and including 0.11 $\mu$m in group A. Thus, another wafer map such as that shown in FIG. 6 may be obtained by reducing the sensitivity of detection of the detectors and/or raising the thresholds for signal processing by the processor, so that defects smaller than a certain size are eliminated as shown in FIG. 6. Thus, by decreasing the detection sensitivity and/or by raising the signal threshold in the processor so that only defects of sizes 0.12 $\mu$m and above are shown and executing the above-described algorithms, one obtains the anomaly classification in the wafer map of FIG. 6. In reference to FIGS. 5 and 6, this will cause groups A, D and E to be eliminated. The defects originally in group F in FIG. 5 is now broken up in to two different groups F' and G in FIG. 6, since the linking defects of sizes 0.09 $\mu$m and 0.1 $\mu$m now no longer appear in FIG. 6. By comparing the two wafer maps in FIGS. 5 and 6, it is possible to characterize the anomaly in group C as a scratch instead of a point defect in the wafer map of FIG. 6 and it is also possible to identify groups F' and G as stemming from the same scratch instead of a shorter scratch F' and a point defect G.

Figure 6:
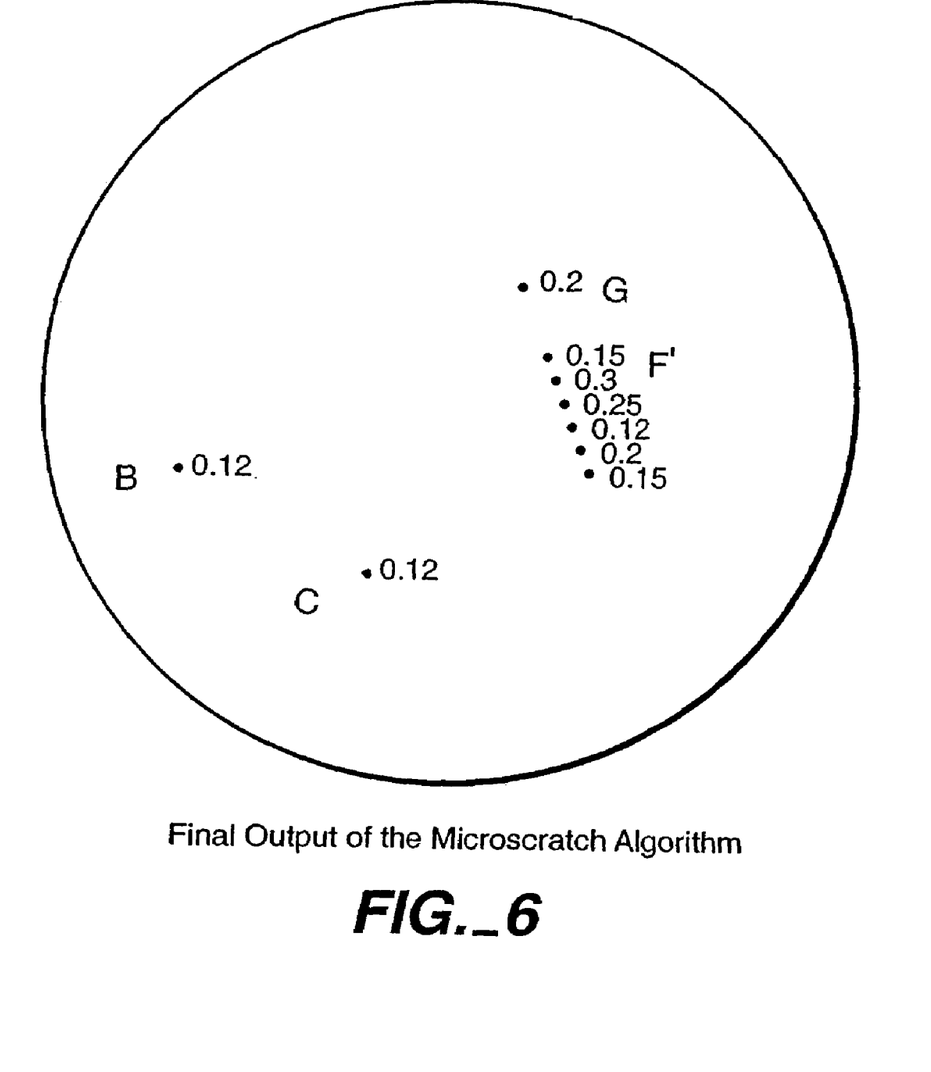
FIG. 6 is a schematic view of the simulated distribution of anomalies on the same sample surface as that illustrated in FIGS. 4 and 5, but using a different detection sensitivity or threshold for analysis to illustrate an embodiment of the invention.

In a conventional system, to avoid the problem that anomalies of sizes of concern are buried amongst a large number of small defects not of concern, the sensitivity of the detector and the threshold of the processor are typically not set to provide the maximum information, so that the defect map provided is typically that shown in FIG. 6. As noted above, if the user is provided only with the wafer map of FIG. 6 without the benefit of the map of FIG. 5, the user would identify the defect in groups C and G as point defects and only group F' as relating to a scratch. Furthermore, group G would appear to be unrelated to group F'. This may lead to different remedies for the wafer cleaning % and CMP processes For example, the wafer map of FIG. 6 may reveal far fewer scratches than there are in reality so that the user may attempt to solve the problem by adjusting the cleaning process rather than altering the CMP process. This may be inadequate to correct the problem. If, however, the group C is also identified to be A scratch and that groups G and F' are identified as stemming from the same scratch, the problem of the scratches on the wafer may be more serious than what will be apparent from a single wafer map of FIG. 6. This may cause the user to adopt a different solution to the problem by also altering the CMP process. For certain users, it may be useful to provide both wafer maps of FIGS. 5 and 6 to provide more information to the user for monitoring or altering the cleaning and CMP processes.

Instead of having to perform the above-described various algorithms twice to arrive at two different wafer maps using different detector sensitivity or processing thresholds, such as the wafer maps of FIGS. 5 and 6, it is possible to simplify the process by performing the algorithms only once to arrive at the wafer map at FIG. 5 at the maximum sensitivity of the detectors, or using the lowest thresholds in processing. As noted above, such map may contain too many small size anomalies not of interest or concern to the user. The size of the anomalies may then be used as the criterion to eliminate the small size defects not of concern to the user, so that only defects above a certain size are retained on the wafer map to be displayed or sent to the user. The size of the anomalies may be indicated by the level of sensitivity or threshold that has been set. For example, by setting the sensitivity of the detector to a certain level, only defects above a certain size would be detected and retained on the wafer map to be displayed or sent to the user. Similarly, where the threshold of the processor has been set to a certain value, only anomalies above a certain size giving rise to output signals above the threshold will be retained on the wafer map to be displayed or sent to the user.

Using the above-described modified and simplified process, it is possible to again arrive at the wafer map of FIG. 6, where the anomalies in group C and groups F' and G will be accurately classified in the same manner when wafer maps of both FIGS. 5 and 6 are obtained. Where one is confident that adequate anomaly information may be obtained without setting the detector sensitivity to the highest level, and/or setting the processing threshold to the lowest level, it is possible to perform the process described before in this application and the above simplified and modified process at a detector sensitivity less then the highest level and/or at a processing threshold higher than the lowest possible level. All such variations are within the scope of the invention.

Figure 7A:
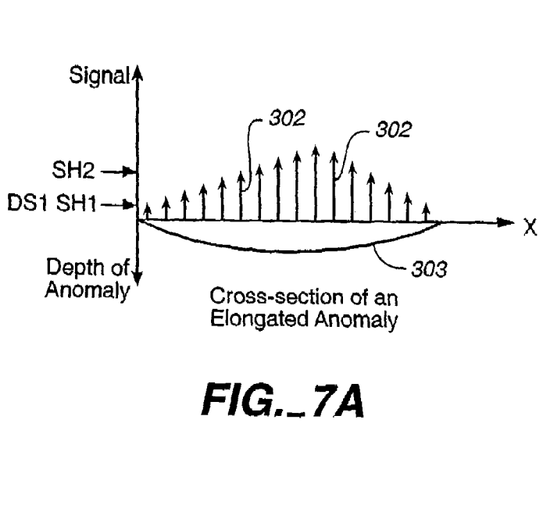
FIGS. 7A and 7B are graphical illustrations of the intensity of radiation detected from elongated anomalies such as scratches to illustrate an embodiment of the invention, where the cross-section of the scratches in FIGS. 7A, 7B are different.
Figure 7B:
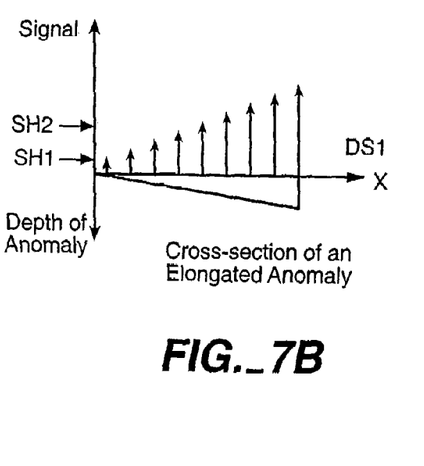
Figure 8A:
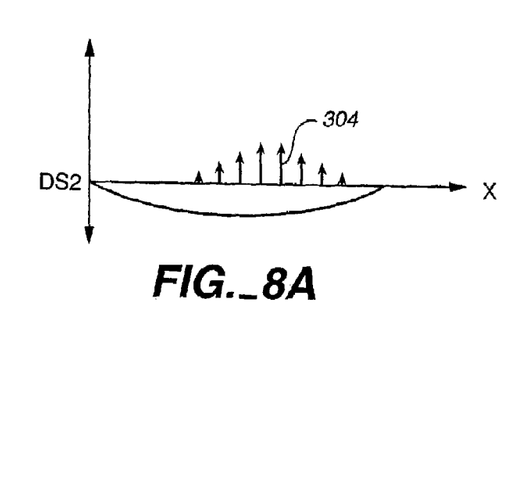
FIGS. 8A and 8B are graphical illustrations of the intensity of radiation detected from the same elongated anomalies as those illustrated in FIGS. 7A, 7B but at a different detection sensitivity or threshold for analysis from that of FIGS. 7A, 7B.

FIGS. 7A and 7B are graphical illustrations of the intensity of radiation detected from elongated anomalies such as scratches to illustrate an embodiment of the invention, where the cross-section of the scratches in FIGS. 7A, 7B are different. As shown in FIG. 7A, the arrows 302 indicate the intensities of radiation detected along a length of a scratch, where the cross-sectional dimensions 303 of the scratch along its length are also shown in FIG. 7A. As shown in FIG. 7A, the scratch has a gentle slope from one end of the scratch to the other, so that the intensity of the detected radiation signal along the length also changes slowly. As will be noted in FIG. 7A, the deeper the portion of the anomaly, the higher will be the intensity of the signal detected by the detector. Also illustrated in FIG. 7A are the two thresholds SH1 and SH2 of the processor for processing. Where the signal processing threshold of the processor has been set to SH1 to provide more information concerning the anomalies, a first classification such as that described above using the various algorithms is obtained. Then using the same intensity data from the detector, the threshold of the processor is set to value SH2 to provide a second classification. A comparison of the two classifications may then be used to provide a better characterization of the defects in the manner described above Alternatively, it is also possible to change the detection sensitivity DS of the detector instead of the threshold of the processor. This is illustrated in FIG. 8A. The signal intensity 302 detected by the detector in FIG. 7A is assumed to be at a higher detector sensitivity DS1. The signal intensity 304 detected by the same detector from the same scratch shown in FIG. 7A but at a lower detection sensitivity DS2 is shown in FIG. 8A. Thus, if the processor processes signal intensities 302 to provide the first classification and the signal intensities 304 to provide a second classification, a comparison of the two classifications will yield useful information in the manner described above. It is possible, of course, to alter both the thresholds SO and detector sensitivities DS to yield similar results. Where only one parameter is altered, it is preferable to alter the threshold SO, since this does not involve scanning the wafer a second time at a different detection sensitivity, which will save time especially in a production environment. While the above described algorithms for clustering or classification are preferable, it will be understood that other cluttering algorithms may be used, such as those described in U.S. Pat. No. 5,991,699, which is incorporated herein by reference in its entirety.

Figure 8B:
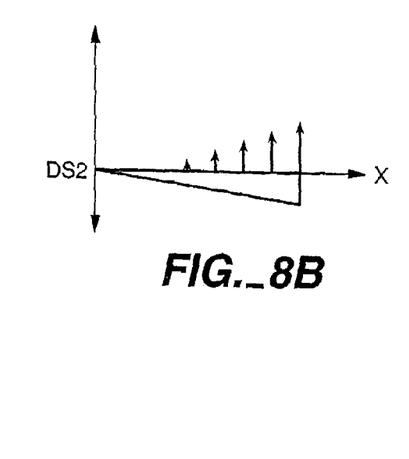

FIGS. 8A and 8B are graphical illustrations of the intensity of radiation detected from the same elongated anomalies as those illustrated in FIGS. 7A, 7B but at a different detection sensitivity or threshold for analysis from that of FIGS. 7A, 7B. FIGS. 7B and 8B illustrate essentially the same considerations as those described above, in reference to FIGS. 7A and 8A, except that the intensity data in FIGS. 7B and 8B are from a scratch that stops abruptly at one end, so that the intensity signal increases gradually along the length of the scratch but then drops off abruptly at one end.

Figure 9:
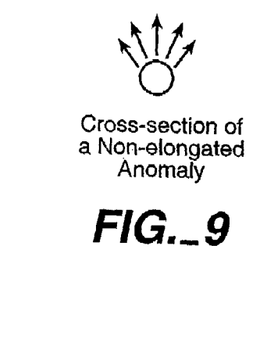
FIG. 9 is a schematic view of the scattering cross-section of an non-elongated anomaly, such as a particle.

FIG. 9 is a schematic view of the scattering cross-section and non-elongated anomaly, such as a particle.

Figure 10:
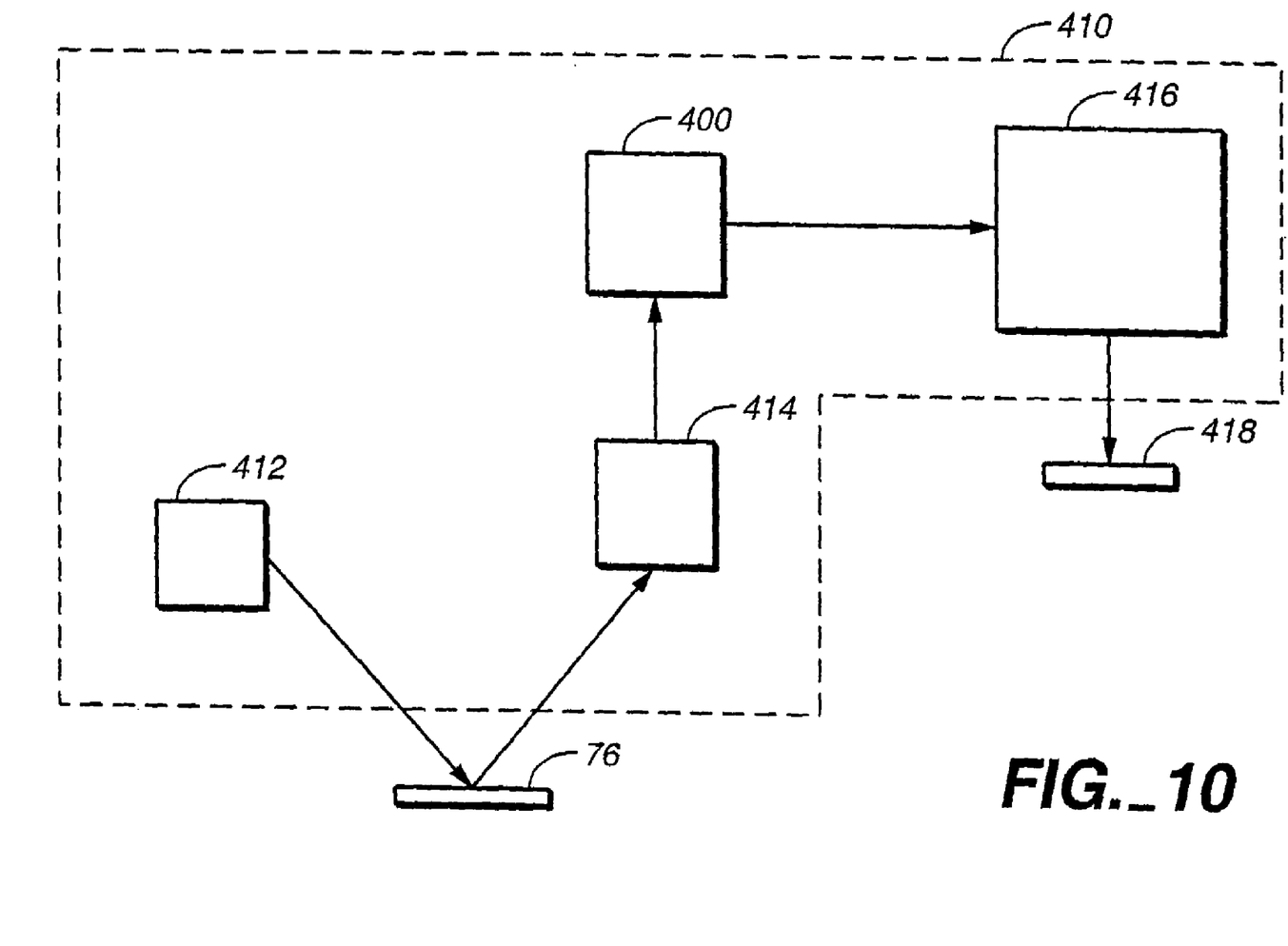
FIG. 10 is a schematic diagram of a sample inspection and processing system 410 illustrating an information flow during the inspection and processing of a sample.

FIG. 10 is a schematic diagram of a sample inspection and processing system 410 illustrating an information flow during the inspection and processing of a sample 76. As shown in FIG. 10, a radiation source and supply system 412 provides radiation to a sample 76 and the radiation provided by system 412 and scattered or reflected by anomalies on sample 76 are collected and detected by collection and detector system 414. The detector output from system 414 is provided to a processor 400 for analysis and classification of the anomalies. The classifications provided by processor 400 are then provided to a processing device 416 for processing sample 76 using information from the classifications. For example, if the classifications provided by processor 400 indicate that the anomalies are mostly particles that can be removed by cleaning process, then a CMP process performed by processing device 416 does not need to be altered for processing samples, such as sample 418. Whereas if the classifications provided by processor 400 indicate a significant number of scratches, processing device 416 may alter its CMP process to reduce the number of scratches caused when processing sample 418.

System 412 may provide any type of radiation to sample 76 from which radiation from anomalies may be detected by system 414 for analysis by processor 400. Thus, source 412 may be an electron source so that system 412, system 414 and processor 400 form an instrument similar to a scanning electron microscope System 412 may also provide electromagnetic radiation in a frequency or wavelength range different from those of instruments in FIGS. 1–3. The electromagnetic radiation provided by system 412 may include x-ray, ultraviolet, infrared or microwave radiation.

At the present state of the art, the inspection system comprising system 412, system 414 and processor 400 typically forms an instrument separate and apart from the processing device 416. Given the trend of integration in the semiconductor equipment industry, it may be desirable to integrate the inspection/detection system together with the processing device to form an integrated system 410, including both the inspection components 412, 414, 400 and the processing component 416 in the same instrument 410.

While the invention has been described above by reference to various embodiments, it will be understood that changes and modifications may be made without departing from the scope of the invention, which is to be defined only by the appended claims and their equivalents. All references referred to herein are incorporated herein by reference in their entirety.

What is claimed is:

1. A method for detecting and classifying anomalies of a surface of a sample of a material suitable for use as a substrate for storage, display or electronic devices, comprising:
supplying radiation to an area of the surface;
detecting radiation from the anomalies associated with the area of the surface to provide an output corresponding to the area by means of a detector; and
analyzing the detector output for anomalies and classifying the anomalies;
wherein the analyzing uses more than one threshold to analyze the detector output and to arrive at at least one classification of the anomalies, said analyzing and classifying comprising processing the output with a first threshold, and classifying the anomalies in a first classification and analyzing the output with a second threshold different from the first threshold, said classifying including applying algorithm(s) to test relationship between anomalies, if any, wherein the output is analyzed with a second threshold without applying the algorithm(s) to test relationship between anomalies.

2. The method of claim 1, said analyzing and classifying comprising using the first classification and the output analyzed with a second threshold to characterize anomalies in the output analyzed with a second threshold.

3. The method of claim 1, said analyzing and classifying comprising characterizing anomalies in the at least one classification as elongated anomalies, area anomalies or point anomalies.

4. The method of claim 3, wherein the elongated anomalies include macroscratches and-microscratches.

5. The method of claim 1, wherein the first threshold is lower than the second threshold, wherein one or more anomalies are classified as scratches when they are classified as scratches at the first threshold whether or not they are classified as scratches at the second threshold.

6. The method of claim 1, wherein the analyzing is performed by means of a processing system and wherein a first threshold used in analyzing anomalies is the lowest practical threshold of the system.

7. The method of claim 1, further comprising displaying only anomalies of sizes that result in detector outputs that exceed the second threshold.

8. The method of claim 1, further comprising displaying only anomalies of sizes that exceed a predetermined value.

9. The method of claim 1, wherein said classifying classifies the anomalies by means of their distribution over the surface.

10. The method of claim 9, wherein said classifying classifies the anomalies detected into two or more of the following three categories: elongated group of anomalies, area group of anomalies or point group of anomalies.

11. The method of claim 10, wherein the elongated group of anomalies comprise macroscratches and microscratches.

12. The method of claim 9, wherein said classifying comprises determining distances between the anomalies detected and grouping into groups the anomalies detected that are within a predetermined distance from one another.

13. The method of claim 12, wherein said classifying classifies the anomalies detected by grouping anomalies into a group only when the number of anomalies in the group exceeds a preset value.

14. The method of claim 12, wherein said determining also determines length and width of a boundary on the surface enclosing at least one group of anomalies detected, and said classifying classifies the anomalies in said at least one group as those forming an elongated group when ratio of the length to the width of the boundary exceeds a preset value, and classifies the anomalies in said at least one group as those forming an area group when ratio of the length to the width of the boundary does not exceed a preset value.

15. The method of claim 14, wherein said classifying classifies the anomalies in an elongated group as those forming a microscratch when the length of the boundary is greater than a preset value.

16. The method of claim 9, wherein said classifying classifies the anomalies in a group as point group of anomalies when the number of anomalies in the group does not exceed a preset value.

17. The method of claim 1, wherein said supplying comprises directing a beam of radiation along a direction to the surface.

18. The method of claim 17, wherein said detecting detects radiation scattered by the anomalies.

19. The method of claim 18, wherein said detecting detects radiation scattered by the anomalies along a direction away from a specular reflection direction of the beam by the surface.

20. The method of claim 19, further comprising controlling a sample processing parameter in response to the at least one classification.

21. A method for detecting and classifying anomalies of a surface of a sample of a material suitable for use as a substrate for storage, display or electronic devices, comprising:

supplying radiation to an area of the surface;
detecting radiation from the anomalies associated with the area of the surface to provide an output corresponding to the area by means of a detector;
analyzing the detector output for anomalies and classifying the anomalies; and
providing classification information concerning classification of anomalies of the surface, said providing comprising processing the detector output with a first threshold, and classifying the anomalies in a first classification;
wherein the analyzing and classifying analyzes the detector output and uses the classification information to arrive at at least one classification of the anomalies, said analyzing and classifying also analyzing the output with a second threshold different from the first threshold, said providing including applying algorithm(s) to test relationship between the anomalies, if any, wherein said analyzing and classifying analyze the detector output with a second threshold without applying the algorithm(s) to test relationship between anomalies.

22. The method of claim 21, said analyzing and classifying comprising using the first classification and the output analyzed with a second threshold to characterize anomalies in the detector output analyzed with a second threshold.

23. A method for detecting and classifying anomalies of a surface of a sample of a material suitable for use as a substrate for storage, display or electronic devices, comprising:
supplying a beam of radiation to an area of the surface;
causing relative motion between the surface and the beam so that the beam traces a spiral path on the surface;
detecting radiation from the anomalies associated with the area of the surface to provide an output corresponding to the area by means of a detector; and
analyzing the detector output for anomalies and classifying the anomalies;
wherein the analyzing uses more than one threshold to analyze the detector output and to arrive at at least one classification of the anomalies, said analyzing and classifying comprising processing the output with a first threshold, and classifying the anomalies in a first classification and analyzing the output with a second threshold different from the first threshold, and wherein the processing of the output with the first threshold and the analyzing of the output with a second threshold are performed independently of one another.

24. The method of claim 23, said analyzing and classifying comprising using the first classification and the output analyzed with a second threshold to characterize anomalies in the output analyzed with a second threshold.

25. The method of claim 23, said analyzing and classifying comprising characterizing anomalies in the at least one classification as elongated anomalies, area anomalies or point anomalies.

26. The method of claim 25, wherein the elongated anomalies include macroscratches and-microscratches.

27. The method of claim 23, wherein the first threshold is lower than the second threshold, wherein one or more anomalies are classified as scratches when they are classified as scratches at the first threshold whether or not they are classified as scratches at the second threshold.

28. The method of claim 23, wherein the analyzing is performed by means of a processing system and wherein a first threshold used in analyzing anomalies is the lowest practical threshold of the system.

29. The method of claim 23, further comprising displaying only anomalies of sizes that result in detector outputs that exceed the second threshold.

30. The method of claim 23, further comprising displaying only anomalies of sizes that exceed a predetermined value.

31. The method of claim 23, wherein said supplying comprises directing a beam of radiation along a direction to the surface.

32. The method of claim 23, further comprising controlling a sample processing parameter in response to the at least one classification.

33. A method for detecting and classifying anomalies of a surface of a sample of a material suitable for use as a substrate for storage, display or electronic devices, comprising:
supplying a beam of radiation to an area of the surface;
causing relative motion between the surface and the beam so that the beam traces a spiral path on the surface;
detecting radiation from the anomalies associated with the area of the surface to provide an output corresponding to the area by means of a detector; and
analyzing the detector output for anomalies and classifying the anomalies;
wherein the analyzing uses more than one threshold to analyze the detector output and to arrive at at least one classification of the anomalies, wherein said classifying classifies the anomalies by means of their distribution over the surface.

34. The method of claim 33, wherein said classifying classifies the anomalies detected into two or more of the following three categories: elongated group of anomalies, area group of anomalies or point group of anomalies.

35. The method of claim 34, wherein the elongated group of anomalies comprise macroscratches and microscratches.

36. The method of claim 33, wherein said classifying comprises determining distances between the anomalies detected and grouping into groups the anomalies detected that are within a predetermined distance from one another.

37. The method of claim 36, wherein said classifying classifies the anomalies detected by grouping anomalies into a group only when the number of anomalies in the group exceeds a preset value.

38. The method of claim 36, wherein said determining also determines length and width of a boundary on the surface enclosing at least one group of anomalies detected, and said classifying classifies the anomalies in said at least one group as those forming an elongated group when ratio of the length to the width of the boundary exceeds a preset value, and classifies the anomalies in said at least one group as those forming an area group when ratio of the length to the width of the boundary does not exceed a preset value.

39. The method of claim 38, wherein said classifying classifies the anomalies in an elongated group as those forming a microscratch when the length of the boundary is greater than a preset value.

40. The method of claim 33, wherein said classifying classifies the anomalies in a group as point group of anomalies when the number of anomalies in the group does not exceed a preset value.

41. The method of claim 31, wherein said detecting detects radiation scattered by the anomalies.

42. The method of claim 41, wherein said detecting detects radiation scattered by the anomalies along a direction away from a specular reflection direction of the beam by the surface.

43. A method for detecting and classifying anomalies of a surface of a sample of a material suitable for use as a substrate for storage, display or electronic devices, comprising:

supplying a beam of radiation to an area of the surface;

causing relative motion between the surface and the beam so that the beam traces a spiral path on the surface;

detecting radiation from the anomalies associated with the area of the surface to provide an output corresponding to the area by means of a detector;

analyzing the detector output for anomalies and classifying the anomalies; and providing classification information concerning classification of anomalies of the surface;

wherein the analyzing and classifying analyzes the detector output and uses the classification information to arrive at at least one classification of the anomalies, said providing comprising processing the detector output with a first threshold, and classifying the anomalies in a first classification, and said analyzing and classifying analyzing the output with a second threshold different from the first threshold, said analyzing and classifying comprising using the first classification and the output analyzed with a second threshold to characterize anomalies in the detector output analyzed with a second threshold.

44. The method of claim 43, said providing including applying algorithm(s) to test relationship between the anomalies, if any, wherein said analyzing and classifying analyze the detector output with a second threshold without applying the algorithm(s) to test relationship between anomalies.

45. A method for detecting and classifying anomalies of a surface of a sample of a material suitable for use as a substrate for storage, display or electronic devices, comprising:

supplying beam of radiation to an area of the surface;

causing relative motion between the surface and the beam so that the beam traces paths on the surface having lengths that are smaller than dimensions of the surface, said paths substantially covering the entire surface;

detecting radiation from the anomalies associated with the area of the surface to provide an output corresponding to the area by means of a detector; and analyzing the detector output for anomalies and classifying the anomalies;

wherein the analyzing uses more than one threshold to analyze the detector output and to arrive at at least one classification of the anomalies, said analyzing and classifying comprising processing the output with a first threshold, and classifying the anomalies in a first classification and analyzing the output with a second threshold different from the first threshold and wherein the processing of the output with the first threshold and the analyzing of the output with a second threshold are performed independently of one another.

46. The method of claim 45, said analyzing and classifying comprising using the first classification and the output analyzed with a second threshold to characterize anomalies in the output analyzed with a second threshold.

47. The method of claim 45, said analyzing and classifying comprising characterizing anomalies in the at least one classification as elongated anomalies, area anomalies or point anomalies.

48. The method of claim 47, wherein the elongated anomalies include macroscratches and-microscratches.

49. The method of claim 45, wherein the first threshold is lower than the second threshold, wherein one or more anomalies are classified as scratches when they are classified as scratches at the first threshold whether or not they are classified as scratches at the second threshold.

50. The method of claim 45, wherein the analyzing is performed by means of a processing system and wherein a first threshold used in analyzing anomalies is the lowest practical threshold of the system.

51. The method of claim 45, further comprising displaying only anomalies of sizes that result in detector outputs that exceed the second threshold.

52. The method of claim 45, further comprising displaying only anomalies of sizes that exceed a predetermined value.

53. The method of claim 45, wherein said classifying classifies the anomalies by means of their distribution over the surface.

54. The method of claim 53, wherein said classifying classifies the anomalies detected into two or more of the following three categories: elongated group of anomalies, area group of anomalies or point group of anomalies.

55. The method of claim 53, wherein the elongated group of anomalies comprise macroscratches and microscratches.

56. The method of claim 53, wherein said classifying comprises determining distances between the anomalies detected and grouping into groups the anomalies detected that are within a predetermined distance from one another.

57. The method of claim 56, wherein said classifying classifies the anomalies detected by grouping anomalies into a group only when the number of anomalies in the group exceeds a preset value.

58. The method of claim 56, wherein said determining also determines length and width of a boundary on the surface enclosing at least one group of anomalies detected, and said classifying classifies the anomalies in said at least one group as those forming an elongated group when ratio of the length to the width of the boundary exceeds a preset value, and classifies the anomalies in said at least one group as those forming an area group when ratio of the length to the width of the boundary does not exceed a preset value.

59. The method of claim 58, wherein said classifying classifies the anomalies in an elongated group as those forming a microscratch when the length of the boundary is greater than a preset value.

60. The method of claim 53, wherein said classifying classifies the anomalies in a group as point group of anomalies when the number of anomalies in the group does not exceed a preset value.

61. The method of claim 45, wherein said supplying comprises directing a beam of radiation along a direction to the surface.

62. The method of claim 61, wherein said detecting detects radiation scattered by the anomalies.

63. The method of claim 62, wherein said detecting detects radiation scattered by the anomalies along a direction away from a specular reflection direction of the beam by the surface.

64. The method of claim 45, further comprising controlling a sample processing parameter in response to the at least one classification.

65. A method for detecting and classifying anomalies of a surface of a sample of a material suitable for use as a substrate for storage, display or electronic devices, comprising:

supplying a beam of radiation to an area of the surface;
causing relative motion between the surface and the beam so that the beam traces paths on the surface having lengths that are smaller than dimensions of the surface, said paths substantially covering the entire surface;
detecting radiation from the anomalies associated with the area of the surface to provide an output corresponding to the area by means of a detector;
analyzing the detector output for anomalies and classifying the anomalies; and
providing classification information concerning classification of anomalies of the surface;
wherein the analyzing and classifying analyzes the detector output and uses the classification information to arrive at at least one classification of the anomalies, said providing comprising processing the detector output with a first threshold, and classifying the anomalies in a first classification, and said analyzing and classifying analyzing the output with a second threshold different from the first threshold, applying algorithm(s) to test relationship between the anomalies, if any, wherein said analyzing and classifying analyze the detector output with a second threshold without applying the algorithm(s) to test relationship between anomalies.

66. The method of claim 65, said analyzing and classifying comprising using the first classification and the output analyzed with a second threshold to characterize anomalies in the detector output analyzed with a second threshold.

* * * * *